US006589519B1

(12) United States Patent
Restle et al.

(10) Patent No.: US 6,589,519 B1
(45) Date of Patent: Jul. 8, 2003

(54) COSMETIC COMPOSITIONS CONTAINING A POLYOXYALKYLENATED AMINOSILICONE BLOCK COPOLYMER AND A CONDITIONER, AND USES THEREOF

(75) Inventors: Serge Restle, Saint-Prix (FR); Danièle Cauwet-Martin, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/486,267

(22) PCT Filed: Aug. 24, 1998

(86) PCT No.: PCT/FR98/01845
§ 371 (c)(1),
(2), (4) Date: Feb. 25, 2000

(87) PCT Pub. No.: WO99/09939
PCT Pub. Date: Mar. 4, 1999

(30) Foreign Application Priority Data

Aug. 25, 1997 (FR) ............................................. 97 10617

(51) Int. Cl.⁷ .............................. A61K 7/06; A61K 7/11
(52) U.S. Cl. .................................................... 424/70.12
(58) Field of Search ...................................... 424/70.12

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,589,578 A | 6/1971 | Kamphausen |
| 3,632,559 A | 1/1972 | Matter et al. |
| 3,874,870 A | 4/1975 | Green et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,172,887 A | 10/1979 | Vanlerberghe et al. |
| 4,217,914 A | 8/1980 | Jacquet et al. |
| 4,349,532 A | 9/1982 | Vanlerberghe et al. |
| 4,381,919 A | 5/1983 | Jacquet et al. |
| 4,591,610 A | 5/1986 | Grollier |
| 4,693,935 A | 9/1987 | Mazurek |
| 4,728,571 A | 3/1988 | Clemens et al. |
| 4,761,273 A | 8/1988 | Grollier et al. |
| 4,839,166 A | 6/1989 | Grollier et al. |
| 4,972,037 A | 11/1990 | Garbe et al. |
| 4,996,049 A | 2/1991 | Haefele et al. |
| 5,089,252 A | 2/1992 | Grollier et al. |
| 5,164,522 A | * 11/1992 | McCarthy et al. ............ 554/39 |
| 5,935,587 A | 8/1999 | Cauwet et al. |

FOREIGN PATENT DOCUMENTS

| | | |
|---|---|---|
| EP | 0 122 324 | 10/1984 |
| EP | 0 337 354 | 10/1989 |
| EP | 0 342 834 | 11/1989 |
| EP | 0 412 704 | 2/1991 |
| EP | 0 412 707 | 2/1991 |
| EP | 0 492 657 | * 1/1992 |
| EP | 0 486 135 | 5/1992 |
| EP | 0 492 657 | 7/1992 |
| EP | 0 582 152 | 2/1994 |
| EP | 0 643 961 | 3/1995 |
| EP | 0 684 041 | 11/1995 |
| FR | 1 492 597 | 8/1967 |

(List continued on next page.)

OTHER PUBLICATIONS

English language Derwent Abstract of EP 0 684 041.
English language Derwent Abstract of FR 2 077 143.
English language Derwent Abstract of FR 2 080 759.
English language Derwent Abstract of FR 2 320 330.
English language Derwent Abstract of FR 2 336 434.
English language abstract of FR 2 368 508.
English language Derwent Abstract of FR 2 383 660.
English language abstract of FR 2 393 573.
English language Derwent Abstract of FR 2 709 954.
English language Derwent Abstract of FR 2 709 955.

Primary Examiner—Alton N. Pryor
(74) Attorney, Agent, or Firm—Finnegan, Henderson, Farabow, Garrett & Dunner, LLP

(57) ABSTRACT

The invention relates to cosmetic compositions comprising, in a cosmetically acceptable medium, at least one conditioner chosen from poly-α-olefins, fluoro oils, fluoro waxes, fluoro gums, carboxylic acid esters, cationic polymers, silicones that are insoluble in the medium, mineral, plant or animal oils and at least one polyoxyalkylenated aminosilicone of (AB)n type, A being a polysiloxane block and B being a polyoxyalkylenated block containing at least one amine group.

This combination gives considerably better cosmetic properties (smoothness, softness) than the properties obtained with one or other of the constituents used alone.

These compositions are used to wash and/or condition the hair.

48 Claims, No Drawings

FOREIGN PATENT DOCUMENTS

| | | |
|---|---|---|
| FR | 1 583 363 | 9/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 270 846 | 12/1974 |
| FR | 2 252 840 | 6/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 5/1986 |
| FR | 2 709 954 | 3/1995 |
| FR | 2 709 955 | * 3/1995 |
| GB | 2114995 | * 9/1983 |
| JP | 59216982 | * 12/1984 |
| JP | 08053663 | * 2/1996 |
| WO | WO 93/11103 | 6/1993 |
| WO | WO 93/23009 | 11/1993 |
| WO | WO 93/23446 | 11/1993 |
| WO | WO 95/00578 | 1/1995 |

* cited by examiner

COSMETIC COMPOSITIONS CONTAINING A POLYOXYALKYLENATED AMINOSILICONE BLOCK COPOLYMER AND A CONDITIONER, AND USES THEREOF

This Application is a 371 of PCT/FR98/01845 filed Aug. 24, 1998.

The present invention relates to novel cosmetic compositions comprising, in a cosmetically acceptable medium, at least one conditioner chosen from poly-α-olefins, fluoro oils, fluoro waxes, fluoro gums, carboxylic acid esters having at least 10 carbon atoms, cationic polymers, silicones that are insoluble in the medium, mineral, plant or animal oils and at least one polyoxyalkylenated aminosilicone of $(AB)_n$ type, A being a polysiloxane block and B being a polyoxyalkylenated block containing at least one amine group.

It is well known that hair which has been sensitized (i.e. damaged and/or embrittled) to varying degrees under the action of atmospheric agents or under the action of mechanical or chemical treatments, such as dyes, bleaches and/or permanent-waving, is often difficult to disentangle and to style, and lacks softness.

It has already been recommended to use conditioners, in particular cationic polymers or silicones, in compositions for washing or caring for keratinous material such as the hair, in order to disentangle the hair and to give it softness and flexibility. However, the cosmetic advantages mentioned above are also unfortunately accompanied, on dried hair, by certain cosmetic effects considered as being undesirable, i.e. lankness of the hairstyle (lack of lightness of the hair), lack of smoothness (hair not uniform from the root to the tip) and insufficient sheen.

In addition, the use of cationic polymers for this purpose has various drawbacks. On account of their high affinity for the hair, some of these polymers become deposited thereon to a large extent during repeated use, and lead to adverse effects such as an unpleasant, laden feel, stiffening of the hair and interfibre adhesion which has an effect on styling. These drawbacks are accentuated in the case of fine hair, which lacks liveliness and body.

In order to improve the conditioning properties of hair products, it has also been recommended (FR-A-2,709,954 and FR-A-2,709,955) to use cosmetic compositions to treat hair containing a combination of a cationic or amphoteric polymer and a nonionic polyoxyalkylenated silicone of (AB)n type, A being a polysiloxane block and B being a polyoxyalkylenated block. However, these compositions are still not entirely satisfactory as regards the smoothness and softness properties imparted to the hair. Furthermore, the hair is made lank after repeated applications.

In summary, it turns out that the current cosmetic compositions containing conditioners are not entirely satisfactory.

The Applicant has now discovered that he combination of a specific aminosilicone with certain conditioners allows these drawbacks to be overcome on account of a synergistic effect.

Thus, after considerable research conducted in this matter, the Applicant has now found that by introducing a polyoxyalkylenated aminosilicone of (AB)n type, A being a polysiloxane block and B being a polyoxyalkylenated block containing at least one amine group, into the compositions, in particular the hair compositions, of the prior art based on conditioners, it is possible to limit, or even to eliminate altogether, the problems generally associated with the use of such compositions, i.e. in particular, the lankness and the lack of smoothness and softness of the hair, while at the same time retaining the other advantageous cosmetic properties which are associated with conditioner-based compositions.

This combination provides cosmetic properties that are considerably better than the properties obtained with one or other of the constituents used alone.

Moreover, when applied to the skin, in particular in the form of a bubble bath or a shower gel, the compositions of the invention provide an improvement in the softness of the skin.

Thus, according to the present invention, novel cosmetic compositions are now proposed comprising, in a cosmetically acceptable medium, at least one polyoxyalkylenated aminosilicone of (AB)n type, A being a polysiloxane block and B being a polyoxyalkylenated block containing at least one amine group and at least one conditioner chosen from poly-α-olefins, fluoro oils, fluoro waxes, fluoro gums, carboxylic acid esters having at least 10 carbon atoms, cationic polymers, silicones that are insoluble in the medium, and mineral, plant or animal oils.

Another subject of the invention relates to a process for treating keratinous material such as the hair, characterized in that it consists in applying cosmetic compositions according to the invention to the said material.

The various subjects of the invention will now be described in detail. All of the meanings and definitions of the compounds used in the present invention given below are valid for all of the subjects of the invention.

The polyoxyalkylenated aminosilicones of (AB)n type, A being a polysiloxane block and B being a polyoxyalkylena-ted block containing at least one amine group, can consist of repeating units of the following general formula:

$$[SiMe_2-O-(SiMe_2O)_x SiMe_2-R-N(H)-R'-O-(C_2H_4O)_a-(C_3H_6O)_b-R'-N(H)-R-] \quad (I)$$

in which:

a is an integer greater than or equal to 1, preferably between 5 and 200 and even more particularly between 5 and 100, b is an integer between 0 and 200, preferably between 4 and 200 and even more particularly between 5 and 100, R, which may be identical or different, represent a divalent organic group which is linked to the adjacent silicon atom via a carbon-silicon bond and to a nitrogen atom, R', which may be identical or different, represent a divalent organic group which is linked to the adjacent oxygen atom via a carbon-oxygen bond and to a nitrogen atom, R is preferably a $C_2$–$C_{12}$ hydrocarbon-based radical optionally containing one or more hetero atoms such as oxygen. More particularly, R denotes an ethylene, linear or branched propylene, linear or branched butylene or —$CH_2CH_2CH_2OCH(OH)CH_2$— radical, R' is a $C_2$–$C_{12}$ hydrocarbon-based radical optionally containing one or more hetero atoms such as oxygen. More particularly, R' denotes a divalent alkylene radical such as, for example, ethylene, linear or branched propylene or linear or branched butylene.

The siloxane blocks generally represent between 50 and 95 mol % relative to the total weight of the silicone, and more particularly between 70 and 85 mol %.

The amine content is generally between 0.02 and 0.5 meq/g of copolymer in a solution at 30% in dipropylene glycol, and more particularly between 0.05 and 0.2.

The weight-average molecular weight of the silicone is preferably between 5000 and 1,000,000 and even more particularly between 10,000 and 200,000.

The block copolymers used in the context of the present invention are prepared by processes known to those skilled in the art, for example by reaction of α,ω-diepoxy- or -dichloro-silicone with an α,ω-diamino polyoxyalkylene.

The polyoxyalkylenated aminosilicone is preferably used in an amount of between 0.01 and 20% by weight relative to the total weight of the composition. More preferably, this amount is between 0.1 and 15% by weight and even more particularly between 0.5 and 10% by weight.

The conditioners can be in liquid, semi-solid or solid form such as, for example, oils, waxes or gums.

According to the invention, the conditioners must be chosen from poly-α-olefins, fluoro oils, fluoro waxes, fluoro gums and carboxylic acid esters having at least 10 carbon atoms, cationic polymers, silicones that are insoluble in the medium, and mineral, plant or animal oils, and the mixtures thereof. The preferred conditioners according to the invention are poly-α-olefins, cationic polymers and silicones that are insoluble in the medium.

The poly-α-olefins are, in particular:
  of hydrogenated or non-hydrogenated polybutene type, and preferably hydrogenated or non-hydrogenated polyisobutene.

Isobutylene oligomers with a molecular weight of less than 1000 and mixtures thereof with polyisobutylenes with a molecular weight of greater than 1000, and preferably between 1000 and 15,000, are preferably used.

As examples of poly-α-olefins which can be used in the context of the present invention, mention may be made more particularly of the products sold under the name Permethyl 99 A, 101 A, 102 A, 104 A (n=16) and 106 A (n=38) by the company Presperse Inc., or alternatively the products sold under the name Arlamol HD (n=3) by the company ICI (n denoting the degree of polymerization),
  of hydrogenated or non-hydrogenated polydecene type.

Such products are sold, for example, under the names Ethylflo by the company Ethyl Corp., and Arlamol PAO by the company ICI.

The carboxylic acid esters are preferably water-insoluble at a concentration of 0.1% by weight at 25° C. The total carbon number of the esters is greater than or equal to 10 and preferably less than 100, and more particularly less than 80. Preferably, they have no surfactant properties.

The acid esters can be mono-, di-, tri- or tetracarboxylic.

Acid esters that are liquid at a temperature of less than or equal to 30° C. are most particularly preferred.

The monocarboxylic acid esters are, in particular, linear or branched, saturated or unsaturated $C_1$–$C_{26}$ aliphatic acid monoesters of linear or branched, saturated or unsaturated, $C_1$–$C_{26}$ aliphatic alcohols, the total carbon number of these esters being greater than or equal to 10.

Among the monoesters, mention may be made of dihydroabietyl behenate; octyldodecyl behenate; isocetyl behenate; cetyl lactate; $C_{12}$–$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isopropyl myristate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; octyldodecyl myristate; oleyl erucate; ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate.

$C_4$–$C_{22}$ di- or tricarboxylic acid esters of $C_1$–$C_{22}$ alcohols and mono-, di- or tricarboxylic acid esters of $C_2$–$C_{26}$ di-, tri-, tetra- or pentahydroxy alcohols can also be used.

Mention may be made in particular of: diethyl sebacate; diisopropyl, sebacate; diisopropyl adipate; di-n-propyl adipate; dioctyl adipate; diisostearyl adipate; dioctyl maleate; glyceryl undecylenate; octyldodecylstearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; trioleyl citrate.

Among the esters mentioned above, it is preferred to use ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate and cetyl octanoate.

The fluoro oils, the fluoro waxes and the fluoro gums are, for example, the perfluoropolyethers described in particular in patent application EP-A-486,135 and the fluorohydrocarbon compounds described in particular in patent application WO 93/11103. The teaching of these two patent applications is included in its entirety in the present application by way of reference.

The term "fluorohydrocarbon compounds" denotes compounds whose chemical structure contains a carbon skeleton in which certain hydrogen atoms have been replaced with fluorine atoms.

The fluoro oils can also be fluorocarbons such as fluoroamines, for example perfluorotributylamine, fluorohydrocarbons, for example perfluorodecahydronaphthalene, fluoro esters and fluoro ethers.

The perfluoropolyethers are sold, for example, under the trade names Fomblin by the company Montefluos and Krytox by the company Du Pont.

Among the fluorohydrocarbon compounds, mention may also be made of fluorine-containing fatty acid esters such as the product sold under the name Nofable FO by the company Nippon Oil.

The oils which can be used in the compositions of the invention are preferably chosen from the group formed by:
  animal or plant oils formed by fatty acid esters of polyols, in particular liquid triglycerides, for example sunflower oil, corn oil, soybean oil, avocado oil, jojoba oil, marrow oil, grapeseed oil, sesame oil, hazelnut oil, fish oils, glyceryl tricaprocaprylate, or plant or animal oils of formula $R_9COOR_{10}$ in which $R_9$ represents a higher fatty acid residue containing from 7 to 29 carbon atoms and $R_{10}$ represents a linear or branched hydrocarbon-based chain containing from 3 to 30 carbon atoms, in particular alkyl or alkenyl, or example purcellin oil or liquid jojoba wax;
  natural or synthetic essential oils such as, for example, eucalyptus oil, hybrid lavender oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;
  hydrocarbons, such as hexadecane and liquid paraffin;
  inorganic acid esters of an alcohol.

The conditioners of cationic polymer type which can be used in accordance with the present invention can be chosen from any of those already known per se as enhancing the cosmetic properties of hair treated with detergent compositions, namely, in particular, those described in patent application EP-A-0,337,354 and in French patent applications FR-A-2,270,846, 2,383,660, 2,598,611, 2,470, 596 and 2,519,863.

Even more generally, for the purposes of the present invention, the expression "cationic polymer" denotes any polymer containing cationic groups and/or groups which can be ionized into cationic groups.

The preferred cationic polymers are chosen from those which contain units containing primary, secondary, tertiary and/or quaternary amine groups which can either form part of the main polymer chain or which can be carried by a lateral substituent that is directly attached thereto.

The cationic polymers used generally have a number-average molecular mass of between 500 and $5 \times 10^6$ approximately, and preferably between $10^3$ and $3 \times 10^6$ approximately.

Among the cationic polymers, mention may be made more particularly of polymers of quaternary polyammonium, polyamino amide and polyamine type. These are known products.

The polymers of the quaternary polyammonium, polyaminoamide and polyamine type which can be used in accordance with the present invention and which may be mentioned in particular are those described in French patents Nos. 2,505,348 or 2,542,997. Among these polymers, mention may be made of:

(1) Quaternized or non-quaternized vinylpyrrolidone/dialkylaminoalkyl acrylate or methacrylate copolymers, such as the products sold under the name "Gafquat" by the company ISP such as, for example, Gafquat 734, 755 or HS100 or alternatively the product known as "Copolymer 937". These polymers are described in detail in French patents 2,077,143 and 2,393,573.

(2) The cellulose ether derivatives containing quaternary ammonium groups, described in French patent 1,492,597, and in particular polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyl-diallylammonium salt.

The commercial products corresponding to this definition are more particularly the products sold under the names "Celquat L 200" and "Celquat H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 or Jaguar C162 by the company Meyhall.

(5) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2,162,025 and 2,280,361;

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2,252,840 and 2,368,508;

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1,583,363.

Among these derivatives, mention may be made more particularly of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of methyldiallylamine or of dimethyldiallylammonium, such as the homopolymers or copolymers containing, as main constituent of the chain, units corresponding to formula (VI) or (VI'):

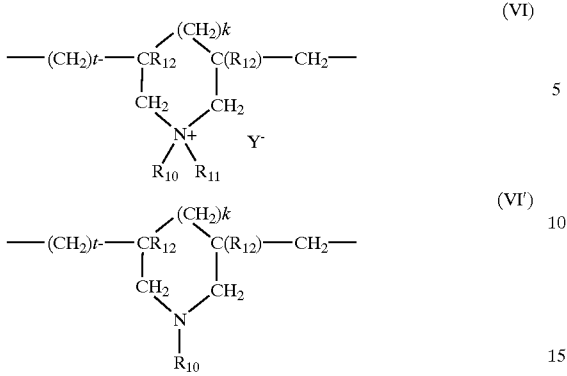

(VI)

(VI')

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 22 carbon atoms, a hydroxyalkyl group in which the alkyl group preferably has 1 to 5 carbon atoms, or a lower amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406.

Among the polymers defined above, mention may be made more particularly of the dimethyldiallyl-ammonium chloride homopolymer sold under the name "Merquat 100" by the company Merck and its homologues of low weight-average molecular mass.

(10) The quaternary diammonium polymer containing repeating units corresponding to the formula:

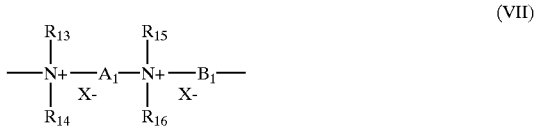

(VII)

in which formula (VII):

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH_2)_n$—CO—D—OC—$(CH_2)_n$— in which D denotes:

a) a glycol residue of formula: —O—Z—O—, where Z denotes a linear or branched hydrocarbon radical or a group corresponding to one of the following formulae:

—(CH$_2$—CH$_2$—O)$_x$—CH$_2$—CH$_2$—

—[CH$_2$—CH(CH$_3$)—O]$_y$—CH$_2$—CH(CH$_3$)— where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon radical, or alternatively the divalent radical

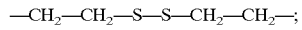

—CH$_2$—CH$_2$—S—S—CH$_2$—CH$_2$—;

d) a ureylene group of formula: —NH—CO—NH—.

Preferably, $X^-$ is an anion such as chloride or bromide.

These polymers generally have a number-average molecular mass of between 1000 and 100,000.

Polymers of this type are described in particular in French patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

According to the invention, polymers chosen from the compounds of formula (VII) in which $R_{13}$, $R_{14}$, $R_{15}$ and $R_{17}$ represent a methyl radical, $A_1$ represents the radical of formula —$(CH_2)_3$— and $B_1$ represents the radical of formula —$(CH_2)_6$— and $X^-$ represents the chloride anion, and the compound of formula (VII) in which $R_{13}$ and $R_{14}$ represent an ethyl radical, $R_{15}$ and $R_{16}$ represent a methyl radical, $A_1$ and $B_1$ represent the radical of formula —$(CH_2)_3$— and $X^-$ represents the bromide anion, can be used more particularly.

(11) Quaternary polyammonium polymers consisting of units of formula (VIII):

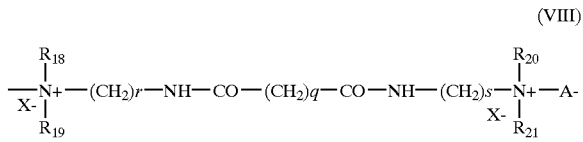

(VIII)

in which formula:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, X denotes a halogen atom, A denotes a dihalide radical or preferably represents —$CH_2$—$CH_2$—O—$CH_2$—$CH_2$—, Such compounds are described in particular in patent application EP-A-122,324.

Among these products, mention may be made, for example, of "Mirapol A 15", "Mirapol AD1", "Mirapol AZ1" and "Mirapol 175" sold by the company Miranol.

(12) Homopolymers or copolymers derived from acrylic or methacrylic acids and containing units:

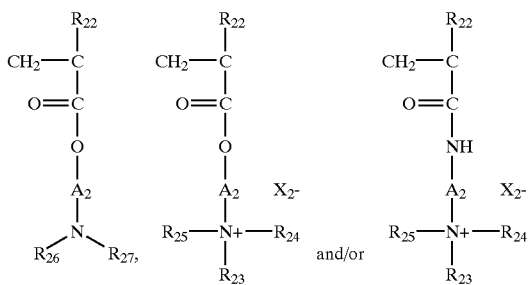

in which the groups $R_{22}$ independently denote H or $CH_3$, the groups $A_1$ independently denote a linear or branched alkyl group of 1 to 6 carbon atoms or a hydroxyalkyl group of 1 to 4 carbon atoms, the groups $R_{23}$, $R_{24}$ and $R_{25}$, which may be identical or different, independently denote an alkyl group of 1 to 18 carbon atoms or a benzyl radical, the groups $R_{26}$ and $R_{27}$ represent a hydrogen atom or an alkyl group of 1 to 6 carbon atoms, $X_2^-$ denotes an anion, for example methosulphate or halide, such as chloride or bromide.

The comonomer(s) which can be used in the preparation of the corresponding copolymers belong to the family of acrylamides, methacrylamides, diacetone acrylamides, acrylamides and methacrylamides substituted on the nitrogen with lower alkyls, alkyl esters, acrylic or methacrylic acids, vinylpyrrolidone or vinyl esters.

(13) Quaternary polymers of vinylpyrrolidone and of vinylimidazole, such as, for example, the products sold under the names Luviquat FC 905, FC 550 and FC 370 by the company BASF.

(14) Polyamines such as Polyquart H sold by Henkel under the reference name "Polyethylene glycol (15) tallow polyamine" in the CTFA dictionary.

(15) Crosslinked methacryloyloxyethyltrimethylammonium chloride polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of the said copolymer in mineral oil can be used more particularly. This dispersion is sold under the name "Salcare SC 92" by the company Allied Colloids.

A crosslinked methacryloyloxyethyltrimethylammonium chloride homopolymer containing about 50% by weight of the homopolymer in mineral oil can also be used. This dispersion is sold under the name "Salcare SC 95" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which can be used in the context of the present invention, it is preferred to use quaternary cellulose ether derivatives such as the products sold under the name "JR 400" by the company Union Carbide Corporation, cyclopolymers, in particular the polymers or copolymers of dimethyldiallylammonium chloride and of acrylamide, sold under the names "Merquat 100", "Merquat 550" and "Merquat S" by the company Merck, cationic polysaccharides and more particularly the guar gum modified with 2,3-epoxypropyltrimethylammonium chloride sold under the name "Jaguar C13S" by the company Meyhall.

The silicones which can be used in accordance with the invention are, in particular, polyorganosiloxanes that are insoluble in the composition and that can be in the form of oils, waxes, resins or gums.

The organopolysiloxanes are defined in greater detail in the book by Walter Noll "Chemistry and Technology of Silicones" (1968) Academic Press. They can be volatile or non-volatile.

When they are volatile, the silicones are more particularly chosen from those having a boiling point of between 60° C. and 260° C., and even more particularly from:

(i) cyclic silicones containing from 3 to 7 and preferably from 4 to 5 silicon atoms. These are, for example, octamethylcyclotetrasiloxane sold in particular under the name "Volatile Silicone 7207" by Union Carbide or "Silbione 70045 V 2" by Rhône-Poulenc, decamethylcyclopentasiloxane sold under the name "Volatile Silicone 7158" by Union Carbide, and "Silbione 70045 V 5" by Rhône-Poulenc, and mixtures thereof.

Mention may also be made of cyclocopolymers of the dimethylsiloxane/methylalkylsiloxane type, such as "Volatile Silicone FZ 3109" sold by the company Union Carbide, of chemical structure:

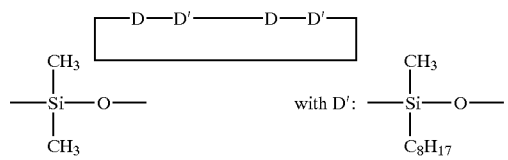

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(i) linear volatile silicones having 2 to 9 silicon atoms and having a viscosity of less than or equal to $5\times10^{-6}$ m$^2$/s at 25° C. This is, for example, decamethyltetrasiloxane sold in particular under the name "SH 200" by the company Toray Silicone. Silicones forming part of this category are also described in the article published in Cosmetics and Toiletries, Vol. 91, January 1976, pp. 27–32, Todd & Byers "Volatile Silicone Fluids for Cosmetics".

Non-volatile silicones, and more particularly polyalkylsiloxanes, polyarylsiloxanes, polyalkylarylsiloxanes, silicone gums and resins, poloyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups having a viscosity of from $5 \times 10^{-6}$ to 2.5 m$^2$/s at 25° C. and preferably $1 \times 10^{-5}$ to 1 m$^2$/s.

Among these polyalkylsiloxanes, mention may be made, in a non-limiting manner, of the following commercial products:

the Silbione oils of the series 47 and 70 047 or the Mirasil oils sold by Rhône-Poulenc, such as, for example, the oil 70 047 V 500 000;

the oils of the Mirasil series sold by the company Rhône-Poulenc;

the oils of the 200 series from the company Dow Corning, such as, more particularly DC200 with a viscosity of 60,000 Cst;

the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhône-Poulenc.

In this category of polyalkylsiloxanes, mention may also be made of the products sold under the names "Abil Wax 9800 and 9801" by the company Goldschmidt, which are poly($C_1$–$C_{20}$)alkylsiloxanes.

The polyalkylarylsiloxanes are chosen particularly from linear and/or branched polydimethyl-methylphenylsiloxanes and polydimethyldiphenylsiloxanes with a viscosity of from $1 \times 10^{-5}$ to $5 \times 10^{-2}$ m$^2$/s at 25° C.

Among these polyalkylarylsiloxanes, mention may be made, by way of example, of the products sold under the following names:

the Silbione oils of the 70 641 series from Rhône-Poulenc;
the oils of the Rhodorsil 70 633 and 763 series from Rhône-Poulenc;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

The silicone gums which can be used in accordance with the invention are, in particular, polydiorganosiloxanes having high number-average molecular masses of between 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:

polydimethylsiloxane
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane.

Products which can be used more particularly in accordance with the invention are mixtures such as:

mixtures formed from a polydimethylsiloxane hydroxylated at the end of the chain (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in SF 1202 Silicone Fluid oil corresponding to decamethylcyclopentasiloxane;

mixtures of two PDMSs of different viscosities, and more particularly of a PDMS gum and a PDMS oil, such as the product SF 1236 from the company General Electric. The product SF 1236 is a mixture of a gum SE 30 defined above, having a viscosity of 20 m$^2$/s, and an oil SF 96, with a viscosity of $5 \times 10^{-6}$ m$^2$/s. This product preferably contains 15% SE 30 gum and 85% SF 96 oil.

The organopolysiloxane resins which can be used in accordance with the invention are crosslinked siloxane systems containing the following units: $R_2SiO_{2/2}$, $R_3SiO_{1/2}$, $RSiO_{3/2}$ and $SiO_{4/2}$ in which R represents a hydrocarbon group having from 1 to 16 carbon atoms or a phenyl group. Among these products, those particularly preferred are the ones in which R denotes a $C_1$–$C_4$ lower alkyl radical, more particularly methyl, or a phenyl radical.

Among these resins, mention may be made of the product sold under the name "Dow Corning 593" or those sold under the names "Silicone Fluid SS 4230 and SS 4267" by the company General Electric, and which are silicones of dimethyl/trimethyl siloxane structure.

Mention may also be made of the resins of the trimethylsiloxysilicate type sold in particular under the names X22-4914, X21-5034 and X21-5037 by the company Shin-Etsu.

The organomodified silicones which can be used in accordance with the invention are silicones as defined above and containing, in their structure, one or more organofunctional groups attached via a hydrocarbon radical.

Among the organomodified silicones, mention may be made of polyorganosiloxanes containing:

polyethylenoxy and/or polypropylenoxy groups optionally containing $C_6$–$C_{24}$ alkyl groups, such as the products known as dimethicone copolyol sold by the company Dow Corning under the name DC 1248 or the oils Silwet L 722, L 7500, L 77 and L 711 from the company Union Carbide and the ($C_{12}$)alkylmethicone copolyol sold by the company Dow Corning under the name Q2 5200;

substituted or unsubstituted amine groups, such as the products sold under the name GP 4 Silicone fluid and GP 7100 by the company Genesee, or the products sold under the names Q2 8220 and Dow Corning 929 or 939 by the company Dow Corning. The substituted amine groups are, in particular, $C_1$–$C_4$ aminoalkyl groups;

thiol groups such as the products sold under the names "GP 72 A" and "GP 71" from Genesee;

alkoxylated groups such as the product sold under the name "Silicone Copolymer F-755" by SWS Silicones and Abil Wax 2428, 2434 and 2440 by the company Goldschmidt;

hydroxyl groups such as the polyorganosiloxanes containing a hydroxyalkyl function, described in French patent application FR-A-85/16334 corresponding to formula (V):

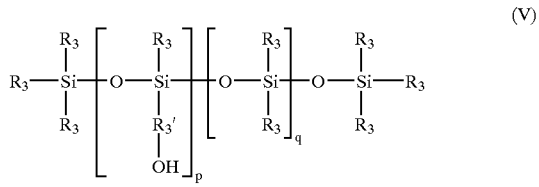

in which the radicals $R_3$, which may be identical or different, are chosen from methyl and phenyl radicals; at least 60 mol % of the radicals $R_3$ denoting methyl; the radical $R'_3$ is a divalent $C_2$–$C_{18}$ hydrocarbon-based alkylene chain unit; p is between 1 and 30 inclusive; q is between 1 and 150 inclusive;

acyloxyalkyl groups such as, for example, the polyorganosiloxanes described in patent U.S. Pat. No. 4,957,732 and corresponding to formula (VI):

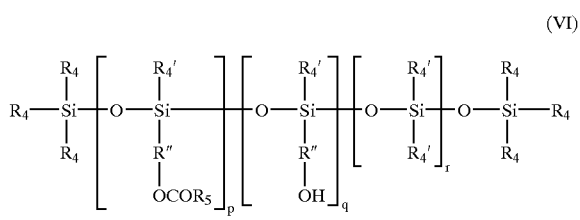

in which:
$R_4$ denotes a methyl, phenyl, —$OCR_5$ or hydroxyl group, it being possible for only one of the radicals $R_4$ per silicon atom to be OH;
$R'_4$ denotes methyl, phenyl; at least 60 mol % of all of the radicals $R_4$ and $R'_4$, denoting methyl;
$R_5$ denotes $C_8$–$C_{20}$ alkyl or alkenyl;
R" denotes a linear or branched, divalent $C_2$–$C_{18}$ hydrocarbon-based alkylene radical;
r is between 1 and 120 inclusive;
p is between 1 and 30;
q is equal to 0 or is less than 0.5 p, p+q being between 1 and 30; the polyorganosiloxanes of formula (VI) can contain groups:

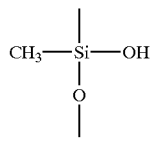

in proportions not exceeding 15% of the sum p+q+r.
anionic groups of carboxylic type, such as, for example, in the products described in patent EP 186 507 from the company Chisso Corporation, or of alkylcarboxylic type, such as those present in the product X-22-3701E from the company Shin-Etsu; 2-hydroxyalkyl sulphonate; 2-hydroxyalkyl thiosulphate such as the products sold by the company Goldschmidt under the names "Abil S201" and "Abil S255".
hydroxyacylamino groups, such as the polyorganosiloxanes described in patent application EP 342 834. Mention may be made, for example, of the product Q2-8413 from the company Dow Corning.

According to the invention, silicones can also be used comprising a polysiloxane portion and a portion consisting of a non-silicone organic chain, one of the two portions constituting the main chain of the polymer, the other being grafted onto the said main chain. These polymers are described, for example, in patent applications EP-A-412, 704, EP-A-412,707, EP-A-640,105, WO 95/00578, EP-A-582,152 and WO 93/23009 and U.S. Pat. Nos. 4,693,935, 4,728,571 and 4,972,037. These polymers are preferably anionic or nonionic.

Such polymers are, for example, copolymers which can be obtained by radical polymerization starting with the monomer mixture consisting of:
a) 50 to 90% by weight of tert-butyl acrylate;
b) 0 to 40% by weight of acrylic acid;
c) 5 to 40% by weight of silicone macromer of formula:

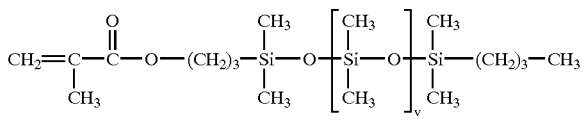

with v being a number ranging from 5 to 700; the weight percentages being calculated relative to the total weight of the monomers.

Other examples of grafted silicone polymers are, in particular, polydimethylsiloxanes (PDMS) onto which are grafted, via a connecting chain unit of thiopropylene type, mixed polymer units of poly(meth)acrylic acid type and of polyalkyl(meth)acrylate type and polydimethylsiloxanes (PDMS) onto which are grafted, via a connecting chain unit of thiopropylene type, polymer units of polyisobutyl(meth) acrylate type.

According to the invention, all of the silicones can also be used in the form of emulsions.

The polyorganosiloxanes which are particularly preferred in accordance with the invention are:
nonvolatile silicones chosen from the family of polyalkylsiloxanes containing dimethylsilyl end groups, such as oils having a viscosity of between 0.2 and 2.5 m²/s at 25° C., such as the oils of the series DC200 from Dow Corning, in particular one with a viscosity of 60,000 Cst, of the series Silbione 70047 and 47 and more particularly the oil 70 047 V 500 000, which are sold by the company Rhône-Poulenc, polyalkylsiloxanes containing dimethylsilanol end groups, such as dimethiconol, or polyalkylarylsiloxanes such as the oil Silbione 70641 V 200 sold by the company Rhône-Poulenc;
mixtures of organopolysiloxanes and of cyclic silicones, such as the product Q2 1401 sold by the company Dow Corning, and the product SF1214 sold by the company General Electric;
mixtures of two PDMSs of different viscosities, in particular of a gum and an oil, such as the product SF 1236 sold by the company General Electric;
the organopolysiloxane resin sold under the name Dow Corning 593;
polysiloxanes containing amine groups, such as amodimethicone or trimethylsilylamodimethicone.

Needless to say, it is possible to use mixtures of conditioners.

According to the invention, the conditioner(s) can represent from 0.001% to 10% by weight, preferably from 0.005% to 7% by weight and even more preferably from 0.01% to 5% by weighs, of the total weight of the final composition.

The compositions of the invention also advantageously contain at least one surfactant, which is generally present in an amount of between 0.1% and 60% by weight approxiamtely, preferably between 3% and 40% and even more preferably between 5% and 30%, relative to the total weight of the composition.

This surfactant can be chosen from anionic, amphoteric, nonionic and cationic surfactants, or mixtures thereof.

The surfactants which are suitable for carrying out the present invention are, in particular, the following:

(i) Anionic surfactant(s)

In the context of the present invention, their nature is not of critical importance.

Thus, as examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, the alkyl or acyl radical of all of these various compounds preferably containing from 8 to 24 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Weakly anionic surfactants can also be used, such as alkyl-D-galactosiduronic acids and their salts, as well as polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, in particular those containing from 2 to 50 ethylene oxide groups, and mixtures thereof.

Among the anionic surfactants, it is preferred according to the invention to use alkyl sulphate salts and alkyl ether sulphate salts and mixtures thereof.

(ii) Nonionic surfactant(s)

The nonionic surfactants are, themselves also, compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric surfactant(s)

The amphoteric surfactants, whose nature is not a critical feature in the context of the present invention, can be, in particular (non-limiting list), aliphatic secondary or tertiary amine derivatives in which the aliphatic radical is a linear or branched chain containing 8 to 22 carbon atoms and containing at least one water-soluble anionic group (for example carboxylate, sulphonate, sulphate, phosphate or phosphonate); mention may also be made of ($C_8$–$C_{20}$)alkylbetaines, sulphobetaines,
($C_8$–$C_{20}$)alkylamido($C_1$–$C_6$)alkylbetaines or
($C_8$–$C_{20}$)alkylamido($C_1$–$C_6$)alkylsulphobetaines.

Among the amine derivatives, mention may be made of the products sold under the name Miranol, as described in U.S. Pat. Nos. 2,528,378 and 2,781,354 and having the structures:

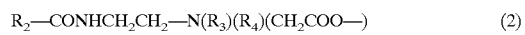

$$R_2\text{—CONHCH}_2\text{CH}_2\text{—N}(R_3)(R_4)(\text{CH}_2\text{COO—}) \qquad (2)$$

in which:

$R_2$ denotes an alkyl radical derived from an acid $R_2$—COOH present in hydrolysed coconut oil, a heptyl, nonyl or undecyl radical, $R_3$ denotes a β-hydroxyethyl group and $R_4$ denotes a carboxymethyl group; and

$$R_5\text{—CONHCH}_2\text{CH}_2\text{—N(B)(C)} \qquad (3)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_5$ denotes an alkyl radical of an acid $R_9$—COOH present in coconut oil or in hydrolysed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid.

By way of example, mention may be made of the cocoamphodiacetate sold under the trade name Miranol C2M concentrate by the company Rhône-Poulenc.

In the compositions in accordance with the invention, mixtures of surfactants are preferably used, and in particular mixtures of anionic surfactants and mixtures of anionic surfactants and of amphoteric or nonionic surfactants. A particularly preferred mixture is a mixture consisting of at least one anionic surfactant and of at least one amphoteric surfactant.

The anionic surfactant used is preferably chosen from ($C_{12}$–$C_{14}$)alkyl sulphates of sodium, of triethanolamine or of ammonium, the ($C_{12}$–$C_{14}$)alkyl ether sulphates of sodium, of triethanolamine or of ammonium oxyethylenated with 2.2 mol of ethylene oxide, sodium cocoyl isethionate and sodium ($C_{14}$–$C_{16}$)-α-olefin sulphonate, and mixtures thereof, with:

either an amphoteric surfactant such as the amine derivatives known as disodium cocoamphodipropionate or sodium cocoamphopropionate, sold in particular by the company Rhône-Poulenc under the trade name "Miranol C2M Conc." as an aqueous solution containing 38% active material, or under the name Miranol C32;

or an amphoteric surfactant of zwitterionic type, such as alkylbetaines, in particular the cocobetaine sold under the name "Dehyton AB 30" as an aqueous solution containing 32% AM by the company Henkel Cationic surfactants can also be used, among which mention may be made in particular (non-limiting list) of: optionally polyoxyalkylenated primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The composition of the invention can also contain at least one additive chosen from thickeners, soluble silicones, surfactants, fragrances, pearlescent agents, preserving agents, silicone or non-silicone sunscreens, proteins, vitamins, ceramides, pseudoceramides, waxes and any other additive conventionally used in the cosmetics field.

These additives are present in the composition according to the invention in proportions which can range from 0 to 20% by weight relative to the total weight of the composition. The precise amount of each additive is readily determined by those skilled in the art depending on its nature and its function.

The compositions in accordance with the invention can be used more particularly for washing or treating keratinous material such as the hair, the skin, the eyelashes, the eyebrows, the nails, the lips or the scalp, and more particularly the hair.

In particular, the compositions according to the invention are detergent compositions such as shampoos, shower gels and bubble baths. In this embodiment of the invention, the compositions comprise a washing base, which is generally aqueous.

The surfactant(s) forming the washing base can be chosen, indifferently, alone or as mixtures, from the anionic, amphoteric, nonionic and cationic surfactants as defined above.

The quantity and quality of the washing base are those which are sufficient to give the final composition satisfactory foaming and/or detergent power.

Thus, according to the invention, the washing base can represent from 2% to 50% by weight, preferably from 10% to 35% by weight and even more preferably from 12% to 25% by weight, of the total weight of the final composition.

The subject of the invention is also a process for treating keratinous material such as the skin or the hair, characterized in that it consists in applying a cosmetic composition as defined above to the keratinous material and then in optionally rinsing with water.

Thus, this process according to the invention allows maintenance of the hairstyle and treatment of, care of, washing of or removal of make-up from the skin, the hair or any other keratinous material.

The compositions of the invention can also be in the form of a rinse-out or leave-in conditioner, in the form of permanent-waving, straightening, dyeing or bleaching compositions, or alternatively in the form of rinse-out compositions to be applied before or after dyeing, bleaching, permanent-waving or straightening the hair, or alternatively between the two steps of a permanent-waving or hair-straightening operation The compositions of the invention can also be in the form of washing compositions for the skin, and in particular in the form of bath or shower solutions or gels or make-up-removing products.

The compositions according to the invention can also be in the form of aqueous or aqueous-alcoholic lotions for skin care and/or hair care.

The cosmetic compositions according to the invention can be in the form of a gel, a milk, a cream, an emulsion, a thickened lotion or a mousse and can be used for the skin, the nails, the eyelashes, the lips and, more particularly, the hair.

The compositions can be packaged in various forms, in particular in vaporizers, pump-dispenser bottles or in aerosol containers in order to ensure application of the composition in vaporized form or in the form of a mousse. Such packaging forms are indicated, for example, when it is desired to obtain a spray, a lacquer or a mousse for treating the hair.

In all of the text hereinabove and hereinbelow, the percentages expressed are on a weight basis.

The invention will now be illustrated more fully with the aid of the examples which follow, which should not be considered as limiting it to the embodiments described. In the examples, AM means active material.

EXAMPLE 1

Three shampoo compositions were prepared, one in accordance with the invention (composition A) and the others comparative (compositions B and C):

|  | A Invention | B Comparative | C Comparative |
|---|---|---|---|
| Sodium lauryl ether sulphate (70/30 $C_{12}/C_{14}$) containing 2.2 mol of ethylene oxide | 17 gAM | 17 gAM | 17 gAM |
| Cocobetaine containing 32% AM (Dehyton AB 30 from Henkel) | 3 gAM | 3 gAM | 3 gAM |
| Polyoxyalkylenated aminosilicone of (AB)n type (Silsoft A843 from OSI) | 1.5 gAM | 2 g | — |
| Cationic guar gum (Jaguar C13S from Meyhall) | 0.5 g | — | 2 g |
| Ethylene glycol distearate | 2.5 g | 2.5 g | 2.5 g |
| Coconut acid monoisopropanolamide | 2 g | 2 g | 2 g |
| NaOH qs pH | 8.5 | 8.5 | 8.5 |
| Demineralized water qs | 100 g | 100 g | 100 g |

(AM=active material)

Shampooing is carried out by applying about 1 g of composition A to 2.7 g locks of pre-moistened bleached hair. The shampoo is worked into a lather, it is left on the hair for 15 minutes and is then rinsed out thoroughly with water. The same procedure as above is carried out with the comparative compositions B and C.

A panel of experts evaluated the smoothness of the dried hair.

The aim of the test used was to classify, by means of a jury, each series of 3 samples as an increasing or decreasing function of the efficacy of disentangling. The 3 locks of the same series are presented simultaneously to the assessor. He or she is asked to classify them from the smoothest to the least smooth. Statistical analysis of the results is carried out using the tables by A. Kramer (Food Technology 17–(12), 124–125 1963).

RESULTS

| Testers | 1 | 2 | 3 | 4 | 5 | 6 | 7 | 8 | 9 | 10 | Σ of the rows |
|---|---|---|---|---|---|---|---|---|---|---|---|
| Lock A | 1 | 1 | 1 | 1 | 1 | 1 | 3 | 1 | 1 | 1 | 12 |
| Lock B | 3 | 2 | 2 | 3 | 3 | 3 | 1 | 2 | 3 | 2 | 24 |
| Lock C | 2 | 3 | 3 | 2 | 2 | 2 | 2 | 3 | 2 | 3 | 24 |

CONCLUSION

For composition A according to the invention, the results obtained with the locks treated with the compositions containing the mixture of the aminosilicone of (AB)n type and of the cationic polymer are significantly better (at the 5% threshold) than those obtained with the other two compositions each containing the compounds used alone.

EXAMPLE 2

Three shampoo compositions were prepared, one in accordance with the invention (composition A) and the others comparative (compositions B and C):

| | A Invention | B Comparative | C Comparative |
|---|---|---|---|
| Sodium lauryl ether sulphate (70/30 $C_{12}/C_{14}$) containing 2.2 mol of ethylene oxide | 17 gAM | 17 gAM | 17 gAM |
| Cocobetaine containing 32% AM (Dehyton AB 30 from Henkel) | 3 gAM | 3 gAM | 3 gAM |
| Polyoxyalkylenated aminosilicone of (AB)n type (Silsoft A843 from OSI) | 1.5 gAM | 2 g | — |
| Hydrogenated polyisobutene (2,2,4,4,6,6,8-heptamethyl-nonane) (Arlamol HD by the company ICI) | 0.5 g | — | 2 g |
| Ethylene glycol distearate | 2.5 g | 2.5 g | 2.5 g |
| Coconut acid monoiso-propanolamide | 2 g | 2 g | 2 g |
| NaOH qs pH | 8.5 | 8.5 | 8.5 |
| Demineralized water qs | 100 g | 100 g | 100 g |

(AM=active material)

Shampooing is carried out by applying about 1 g of composition A to 2.7 g locks of pre-moistened bleached hair. The shampoo is worked into a lather, it is left on the hair for 15 minutes and is then rinsed out thoroughly with water. The same procedure as above is carried out with the comparative compositions B and C.

A panel of experts evaluated the smoothness of the dried hair.

The aim of the test used was to classify, by means of a jury, each series of 3 samples as an increasing or decreasing function of the efficacy of disentangling. The 3 locks of the same series are presented simultaneously to the assessor. He or she is asked to classify them from the smoothest to the least smooth. Statistical analysis of the results is carried out using the tables by A. Kramer (Food Technology 17–(12), 124–125 1963).

RESULTS

| Testers | 1 | 2 | 3 | 4 | 5 | 6 | 7 | 8 | 9 | 10 | Σ of the rows |
|---|---|---|---|---|---|---|---|---|---|---|---|
| Lock A | 1 | 1 | 1 | 1 | 1 | 1 | 1 | 1 | 1 | 1 | 10 |
| Lock B | 2 | 3 | 2 | 3 | 3 | 3 | 3 | 3 | 2 | 3 | 27 |
| Lock C | 3 | 2 | 3 | 2 | 2 | 2 | 2 | 2 | 3 | 2 | 23 |

CONCLUSION

For composition A according to the invention, the results obtained with the locks treated with the compositions containing the mixture of the aminosilicone of (AB)n type and of the poly-α-olefin are significantly better (at the 5% threshold) than those obtained with the other two compositions each containing the compounds used alone.

EXAMPLE 3

A shampoo composition in accordance with the invention is prepared:

| | |
|---|---|
| Ammonium lauryl ether sulphate containing 2.2 mol of ethylene oxide | 14 gAM |
| Sodium cocoamphodiacetate (Miranol C2M Conc. from Rhodia Chimie) | 2.5 gAM |
| Polyoxyalkylenated aminosilicone of (AB)n type (Silsoft A843 from OSI) | 1.5 gAM |
| Isopropyl palmitate | 1 g |
| Ethylene glycol distearate | 2.5 g |
| Coconut acid monoisopropanolamide | 2 g |
| HCl qs pH | 7.5 |
| Demineralized water qs | 100 g |

(AM=active material)

EXAMPLE 4

A shampoo composition in accordance with the invention is prepared:

| | |
|---|---|
| Sodium lauryl ether carboxylate Akypo RLM 45 from Chem Y | 15 gAM |
| Alkyl polyglycoside (KAG 40 from KAO) | 3 gAM |
| Polyoxyalkylenated aminosilicone of (AB)n type (Silsoft A843 from OSI) | 2 gAM |
| Isopropyl stearate | 2 g |
| Fragrance, preserving agent | qs |
| HCl qs pH | 7 |
| Demineralized water qs | 100 g |

(AM=active material)

EXAMPLE 5

A conditioner of the following composition is prepared:

| | |
|---|---|
| Hydroxyethylcellulose sold under the name Natrosol 250 HHR by Aqualon | 1 g |
| Cetylstearyl alcohol/cetylstearyl alcohol 30 EO mixture | 3 g |
| Polydimethylsiloxane (DC200–60000 cst from Dow Corning) | 3 g |
| Silsoft A843 | 2 g |
| Preserving agent, fragrance qs | |
| Water qs | 100 g |

EXAMPLE 6

An oxidizing composition for the permanent reshaping or straightening of the hair, of the following composition, is prepared:

| | |
|---|---|
| Cetylstearyl alcohol/cetylstearyl alcohol 30 EO mixture | 4 g |
| Alkyl ether carboxylic acid monoethanolamide containing 2 mol of ethylene oxide (Aminol A 15 from Chem Y) | 1 g |
| Silsoft A843 | 1 gAM |
| Copolymer of trimethylammonium methacrylate chloride and of acrylamide (Salcare SC92 from Allied Colloid) | 0.5 gAM |
| Hydrogen peroxide | 2.5 g |
| Diethylenetriaminepentaacetic acid, pentasodium salt | 0.05 g |
| Stabilizer | 0.06 g |
| Phosphoric acid | 0.17 g |
| Demineralized water qs | 100 g |

EXAMPLE 6

An oxidizing composition for the permanent reshaping or straightening of the hair, of the following composition, is prepared:

| | |
|---|---|
| Cetyl alcohol | 2 g |
| Stearyl alcohol containing 2.2 mol of ethylene oxide | 0.5 g |
| Silsoft A843 | 1 gAM |
| Hydrogen cetearyl phosphate/cetearyl alcohol | 3.2 g |
| Liquid petroleum jelly | 3 g |
| Hydrogen peroxide | 2.5 g |
| Diethylenetriaminepentaacetic acid, pentasodium salt | 0.15 g |
| Stabilizer | 0.06 g |
| Phosphoric acid | 0.17 g |
| Demineralized water qs | 100 g |

What is claimed is:

1. A cosmetic composition comprising, in a cosmetically acceptable medium,
   a) at least one polyoxyalkylenated aminosilicone having the structure $(AB)_n$, wherein A is a polysiloxanes block and B is a polyoxyalkylenated block containing at least one amine group, and
   b) at least one conditioner chosen from poly-α-olefins, fluoro oils, fluoro waxes, fluoro gums, carboxylic acid esters having at least 10 carbon atoms, cationic polymers, silicones that are insoluble in the cosmetically acceptable medium, mineral oils, plant oils, and animal oils, wherein said at least one polyoxyalkylenated aminosilicone is comprised of repeating units of the following general formula (I):

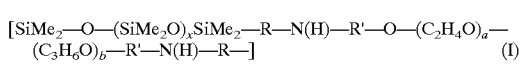

in which:
   a is an integer greater than or equal to 1,
   b is an integer between 0 and 200,
   R, which may be identical or different, represents a divalent organic group which is linked to the adjacent silicon atom via a carbon-silicon bond and to a nitrogen atom, and R', which may be identical or different, represents a divalent organic group which is linked to the adjacent oxygen atom via a carbon-oxygen bond and to a nitrogen atom, wherein x is an integer chosen such that the siloxane block represents between 50 and 95 mol % relative to the total weight of the polyoxyalkylenated aminosilicone.

2. A composition according to claim 1, wherein a ranges from 5 to 200.

3. A composition according to claim 1, wherein a ranges from 5 to 100.

4. A composition according to claim 1, wherein b ranges from 4 to 200.

5. A composition according to claim 1, wherein b ranges from 5 to 100.

6. A composition according to claim 1, wherein the radicals R and R', which may be identical or different, are chosen from $C_2$–$C_{12}$ hydrocarbon-based radicals.

7. A composition according to claim 6, wherein the radicals R and R', which may be identical or different, denote a divalent alkylene radical.

8. A composition according to claim 6, wherein the radicals R and R' contain one or more hetero atoms.

9. A composition according to claim 8, wherein the hetero atoms are oxygen atoms.

10. A composition according to claim 6, wherein the radical R denotes an ethylene radical, a linear propylene radical, a branched propylene radical, a linear butylene radical, a branched butylene radical, or a —$CH_2CH_2CH_2OCH(OH)CH_2$— radical.

11. A composition according to claim 6, wherein the radical R' denotes an ethylene radical, a linear propylene radical, a branched propylene radical, a linear butylene radical, or a branched butylene radical.

12. A composition according to claim 1, wherein the poly-α-olefins are chosen from hydrogenated polybutene, non-hydrogenated polybutene, hydrogenated polydecene, non-hydrogenated polydecene, and mixtures thereof.

13. A composition according to claim 1, wherein the carboxylic acid esters are chosen from dihydroabietyl behenate, octyldodecyl behenate, isocetyl behenate, cetyl lactate, $C_{12}$–$C_{15}$ alkyl lactate, isostearyl lactate, lauryl lactate, linoleyl lactate, oleyl lactate, (iso)stearyl octanoate, isocetyl octanoate, octyl octanoate, cetyl octanoate, decyl oleate, isocetyl isostearate, isocetyl laurate, isocetyl stearate, isodecyl octanoate, isodecyl oleate, isononyl isononanoate, isostearyl palmitate, methylacetyl ricinoleate, myristyl stearate, octyl isononanoate, 2-ethylhexyl isononate, octyl palmitate, octyl pelargonate, octyl stearate, octyldodecyl erucate, octyldodecyl myristate, oleyl erucate, ethyl and isopropyl palmitates, 2-ethylhexyl palmitate, 2-octyldecyl palmitate, alkyl myristates, hexyl stearate, butyl stearate, isobutyl stearate, dioctyl malate, hexyl laurate, 2-hexyldecyl laurate, diethyl sebacate, diisopropyl sebacate, diisopropyl adipate, di-n-propyl adipate, dioctyl adipate, diisostearyl adipate, dioctyl maleate, glyceryl undecylenate, octyldodecylstearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate dicaprate, tridecyl erucate, triisopropyl citrate, triisostearyl citrate, glyceryl trilactate, glyceryl trioctanoate, trioctyldodecyl citrate, trioleyl citrate, and mixtures thereof.

14. A composition according to claim 1, wherein the fluoro oils, fluoro waxes, and fluoro gums are chosen from perfluoropolyethers, fluorohydrocarbon compounds, and mixtures thereof.

15. A composition according to claim 1, wherein the cationic polymers are chosen from quaternary cellulose ether derivatives, cyclopolymers, cationic polysaccharides, and mixtures thereof.

16. A composition according to claim 15, wherein the cyclopolymers are chosen from diallyldimethylammonium chloride homopolymers and copolymers of diallyldimethylammonium chloride and acrylamide.

17. A composition according to claim 15, wherein the quaternary cellulose ether derivatives are chosen from hydroxyethylcelluloses which have reacted with an epoxide substituted with a trimethylammonium group.

18. A composition according to claim 15, wherein the cationic polysaccharides are chosen from guar gums modified with a 2,3-epoxypropyltrimethylammonium salt.

19. A composition according to claim 1, wherein the silicones are chosen from polyorganosiloxanes that are insoluble in the composition and that are in the form of oil waxes, resins, or gums.

20. A composition according to claim 19, wherein the polyorganosiloxanes are chosen from polyalkylsiloxanes containing trimethylsilyl end groups, polyalkylsiloxanes containing dimethylsilanol end groups, polyalkylarylsiloxanes, mixtures of two polydimethylsiloxanes consisting of a gum and of an oil of different viscosities, mixtures of organosiloxanes and of cyclic silicones, organopolysiloxane resins, and mixtures thereof.

21. A composition according to claim 19, wherein the polyorganosiloxanes are non-volatile polyorganosiloxanes chosen from polyalkylsiloxanes, polyarylsiloxanes, polyalkylarylsiloxanes, silicone gums, silicone resins, polyorganosiloxanes modified with organofunctional groups, and mixtures thereof.

22. A composition according to claim 21, wherein the polyalkylsiloxanes are chosen from polydimethylsiloxanes containing trimethylsilyl end groups, polydimethylsiloxanes containing dimethylsilanol end groups, poly($C_1$–$C_{20}$) alkylsiloxanes, and mixtures thereof.

23. A composition according to claim 21, wherein the polyalkylarylsiloxane are chosen from polydimethylmethylphenylsiloxanes, linear polydimethyldiphenyl siloxanes with a viscosity of between $1 \times 10^{-5}$ and $5 \times 10^{-2}$ m$^2$/s at 25° C., branched polydimethyldiphenylsiloxanes with a viscosity of between $1 \times 10^{-5}$ and $5 \times 10^{-2}$ m$^2$/s at 25° C., and mixtures thereof.

24. A composition according to claim 21, wherein the silicone gums are chosen from polydiorganosiloxanes having number-average molecular masses of between 200,000 and 1,000,000, used alone or in the form of a mixture in a solvent.

25. A composition according to claim 21, wherein the silicone resins are chosen from resins comprising the following units: $R_3SiO_{1/2}$, $R_2SiO_{2/2}$, $RSiO_{3/2}$, and $SiO_{4/2}$ in which R, which may be identical or different, represents a hydrocarbon-based group having from 1 to 16 carbon atoms, a phenyl group, or mixtures thereof.

26. A composition according to claim 21, wherein the polyorganosiloxanes modified with organofunctional groups are chosen from silicones containing one or more organofunctional groups attached via a hydrocarbon-based radical.

27. A composition according to claim 21, wherein the silicone gums are chosen from polydimethylsiloxane, polydimethylsiloxane/methylvinylsiloxanes, polydimethylsiloxane/diphenylsiloxane, polydimethylsiloxane/phenylmethylsiloxane, polydimethylsiloxane/diphenylsiloxane/methyl-vinylsiloxanes, mixtures formed from a polydimethylsiloxane hydroxylated at the end of the chain and from a cyclic polydimethylsiloxane, mixtures formed from a polydimethylsiloxane gum and from a cyclic silicone, mixtures of polydimethylsiloxanes of different viscosities, and mixture thereof.

28. A composition according to claim 21, wherein the polyorganosiloxanes modified with organofunctional groups are chosen from polyorganosiloxanes containing:

a) polyethylenoxy or polypropylenoxy groups, and mixtures thereof;

b) substituted or unsubstituted amine groups;

c) thiol groups;

d) alkoxylated groups;

e) hydroxyalkyl groups corresponding to the following formula (V):

$$R_3-\underset{\underset{R_3}{|}}{\overset{\overset{R_3}{|}}{Si}}-O-\left[\underset{\underset{R_3'}{|}}{\overset{\overset{R_3}{|}}{Si}}-O\right]\left[\underset{\underset{OH}{|}}{\overset{\overset{}{}}{}}\right]_p\left[\underset{\underset{R_3}{|}}{\overset{\overset{R_3}{|}}{Si}}-O\right]_q-\underset{\underset{R_3}{|}}{\overset{\overset{R_3}{|}}{Si}}-R_3 \quad (V)$$

in which $R_3$, which may be identical or different, is chosen from methyl and phenyl radicals, wherein at least 60 mol % of the radicals $R_3$ are methyl, $R'_3$, which may be identical or different, is a divalent $C_2$–$C_{18}$ hydrocarbon-based alkylene chain unit, p ranges from 1 to 30, and q ranges from 1 to 150;

f) acyloxyalkyl groups corresponding to the following formula (VI):

$$R_4-\underset{\underset{R_4}{|}}{\overset{\overset{R_4}{|}}{Si}}-O-\left[\underset{\underset{OCOR_5}{|}}{\overset{\overset{R_4'}{|}}{Si}}-O\right]_p\left[\underset{\underset{OH}{|}}{\overset{\overset{R_4'}{|}}{Si}}-O\right]_q\left[\underset{\underset{R_4'}{|}}{\overset{\overset{R_4'}{|}}{Si}}-O\right]_r-\underset{\underset{R_4}{|}}{\overset{\overset{R_4}{|}}{Si}}-R_4 \quad (VI)$$

in which:

$R_4$, which may be identical or different, denotes a methyl, phenyl, —$OCOR_5$, or hydroxyl group, wherein only one of the radicals $R_4$ per silicon atom are —OH, $R'_4$, which may be identical or different, denotes a methyl or phenyl group, and wherein at least 60 mol % of all of the radicals $R_4$ and $R'_4$ denote methyl, $R_5$, which may be identical or different, denotes $C_8$–$C_{20}$ alkyl or alkenyl, R", which may be identical or different, denotes a linear or branched, divalent $C_2$–$C_{18}$ hydrocarbon-based alkylene radical, r ranges from 1 to 120, p ranges from 1 to 30, q is equal to 0 or is less than p/2, wherein p+q ranges from 1 to 30, and wherein the polyorganosiloxanes of formula (VI) optionally contain groups:

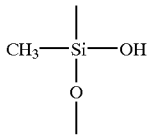

in proportions not exceeding 15% of the sum p+q+r;

g) alkylcarboxylic groups;

h) 2-hydroxyalkyl sulphonate groups;

i) 2-hydroxyalkyl thiosulphonate groups; and j) hydroxyacylamino groups.

29. A composition according to claim 1, further comprising at least one surfactant chosen from anionic surfactants, cationic surfactants, nonionic surfactants, and amphoteric surfactants.

30. A composition according to claim 29, wherein the surfactant is present in an amount ranging from 0.1% to 40% by weight, relative to the total weight of the composition.

31. A composition according to claim 29, wherein the at least one surfactant is present in an amount ranging from 3% to 40% by weight, relative to the total weight of the composition.

32. A composition according to claim 29, wherein the at least one surfactant is present in an amount ranging from 5% to 30% by weight, relative to the total weight of the composition.

33. A composition according to claim 1, wherein the at least one conditioner is present in an amount ranging from 0.001% to 10% by weight, relative to the total weight of the composition.

34. A composition according to claim 1, wherein the at least one conditioner is present in an amount ranging from 0.005% to 7% by weight, relative to the total weight of the composition.

35. A composition according to claim 1, wherein the at least one conditioner is present in an amount ranging from 0.01% to 5% by weight, relative to the total weight of the composition.

36. A composition according to claim 1, wherein the composition is a shampoo, a conditioner, a composition for permanent-waving the hair, a composition for straightening the hair, a composition for dyeing the hair, a composition for bleaching the hair, a rinse-out composition to be applied between the two steps of a permanent-waving or hair-straightening operation, or a washing composition for the body.

37. A composition according to claim 1, wherein the weight average molecular weight of the aminosilicone ranges from 5,000 to 1,000,000.

38. A composition according to claim 1, wherein the weight average molecular weight of the aminosilicone ranges from 10,000 to 200,000.

39. A composition according to claim 1, wherein the siloxane blocks represent 70 to 85 mol %, relative to the total weight of the aminosilicone.

40. A composition according to claim 37, wherein the siloxane blocks represent 50 to 95 mol %, relative to the total weight of the aminosilicone.

41. A composition according to claim 38, wherein the siloxane blockS represent 50 to 95 mol %, relative to the total weight of the aminosilicone.

42. A composition according to claim 37, wherein the siloxane blocks represent 70 to 85 mol %, relative to the total weight of the aminosilicone.

43. A composition according to claim 38, wherein the siloxane blocks represent 70 to 85 mol %, relative to the total weight of the aminosilicone.

44. A composition according to claim 13, wherein the alkyl myristates are chosen from isopropyl, butyl, cetyl and 2-octyldodecyl myristate.

45. A method for treating keratinous substances comprising applying a cosmetic composition comprising, in a cosmetically acceptable medium, a) at least one polyoxyalkylenated aminosilicone having the structure $(AB)_n$, wherein A is a polysiloxane block and B is a polyoxyalkylenated block containing at least one amine group, and b) at least one conditioner chosen from poly-α-olefins, fluoro oils, fluoro waxes, fluoro gums, carboxylic acid esters having at least 10 carbon atoms, cationic polymers, silicones that are insoluble in the medium, mineral oils, plant oils, and animal oils, to the keratinous substances, wherein said at least one polyoxyalkylenated aminosilicone is comprised of repeating units of the following general formula (I):

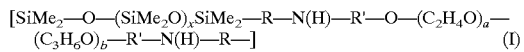

in which:

a is an integer greater than or equal to 1, b is an integer between 0 and 200,

R, which may be identical or different, represents a divalent organic group which is linked to the adjacent silicon atom via a carbon-silicon bond and to a nitrogen atom, and R', which may be identical or different, represents a divalent organic group which is linked to the adjacent oxygen atom via a carbon-oxygen bond and to a nitrogen atom, wherein x is an integer chosen such that the siloxane block represents between 50 and 95 mol % relative to the total weight of the polyoxyalkylenated aminosilicone.

46. A method according to claim 45, wherein the keratinous substances are hair.

47. A method for increasing the softness and/or smoothness of keratinous substances comprising applying a cosmetic composition comprising, in a cosmetically acceptable medium, a) at least one polyoxyalkylenated aminosilicone having the structure $(AB)_n$, wherein A is a polysiloxane block and B is a polyoxyalkylenated block containing at least one amine group, and b) at least one conditioner chosen from poly-α-olefins, fluoro oils, fluoro waxes, fluoro gums, carboxylic acid esters having at least 10 carbon atoms, cationic polymers, silicones that are insoluble in the medium, mineral oils, plant oils, and animal oils, to the keratinous substances, wherein said at least one polyoxyalkylenated aminosilicone is comprised of repeating units of the following general formula (I):

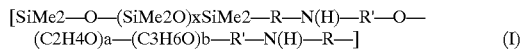

in which:

a is an integer greater than or equal to 1, b is an integer between 0 and 200,

R, which may be identical or different, represents a divalent organic group which is linked to the adjacent silicon atom via a carbon-silicon bond and to a nitrogen atom, and R', which may be identical or different, represents a divalent organic group which is linked to the adjacent oxygen atom via a carbon-oxygen bond and to a nitrogen atom, wherein x is an integer chosen such that the siloxane block represents between 50 and 95 mol % relative to the total weight of the polyoxyalkylenated aminosilicone.

48. A method according to claim 47, wherein the keratinous substances are hair.

* * * * *

UNITED STATES PATENT AND TRADEMARK OFFICE
CERTIFICATE OF CORRECTION

PATENT NO. : 6,589,519 B1
DATED : July 8, 2003
INVENTOR(S) : Serge Restle et al.

It is certified that error appears in the above-identified patent and that said Letters Patent is hereby corrected as shown below:

Column 21,
Line 45, "polysiloxanes" should read -- polysiloxane --.

Column 23,
Line 19, "oil" should read -- oils, --.
Line 42, "polyalkylarylsiloxane" should read -- polyalkylarylsiloxanes --.

Column 24,
Line 6, "mixture" should read -- mixtures --.
Lines 21-27, in formula (V),

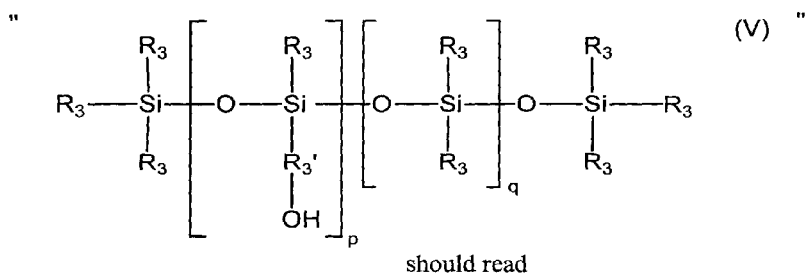

should read

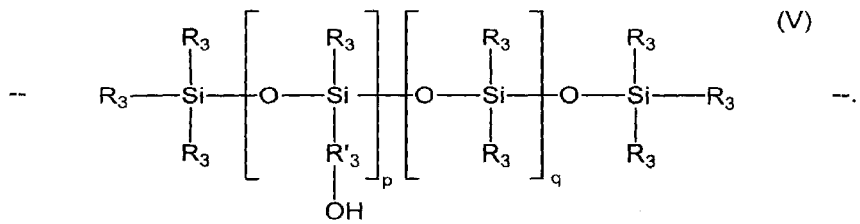

Lines 42-48, in formula (VI),

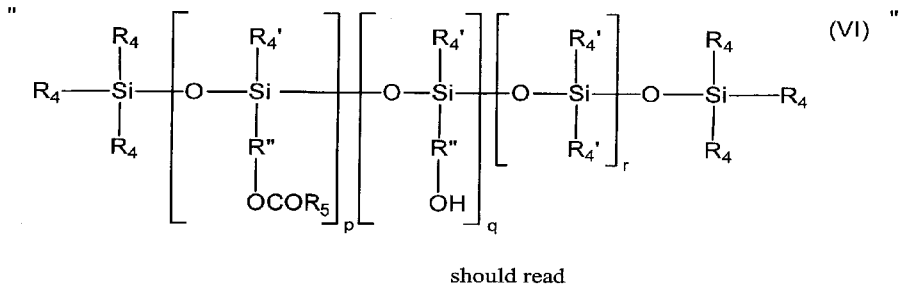

should read

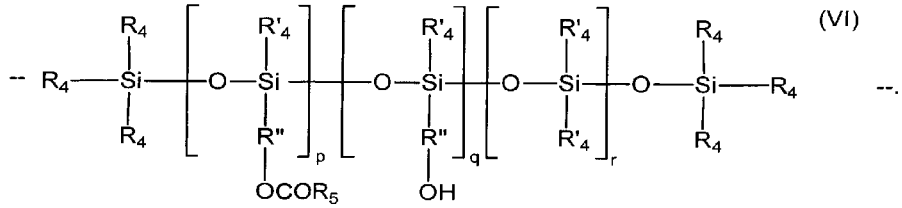

UNITED STATES PATENT AND TRADEMARK OFFICE
CERTIFICATE OF CORRECTION

PATENT NO. : 6,589,519 B1
DATED : July 8, 2003
INVENTOR(S) : Serge Restle et al.

It is certified that error appears in the above-identified patent and that said Letters Patent is hereby corrected as shown below:

<u>Column 25,</u>
Line 66, "blockS" should read -- blocks --.

<u>Column 26,</u>
Lines 62-63, in formula (I), "[SiMe2-O-(SiMe2O)xSiMe2-R-N(H)-R'-O-(C2H4O) a-(C3H6O)b-R'-N(H)-R-]" should read -- [SiMe$_2$-O-(SiMe$_2$O)$_x$SiMe$_2$-R-N(H)-R'-O-(C$_2$H$_4$O)$_a$-(C$_3$H$_6$O)$_b$-R'-N(H)-R-] --.

Signed and Sealed this

Twenty-first Day of October, 2003

JAMES E. ROGAN
*Director of the United States Patent and Trademark Office*